(12) United States Patent
Mei et al.

(10) Patent No.: US 9,993,203 B2
(45) Date of Patent: Jun. 12, 2018

(54) ELECTRONIC STICKERS WITH MODULAR STRUCTURES

(71) Applicant: VivaLnk Limited (Cayman Islands), Santa Clara, CA (US)

(72) Inventors: Junfeng Mei, Sunnyvale, CA (US); Jiang Li, Cupertino, CA (US)

(73) Assignee: VivaLnk, Inc., Santa Clara, CA (US)

( * ) Notice: Subject to any disclaimer, the term of this patent is extended or adjusted under 35 U.S.C. 154(b) by 758 days.

(21) Appl. No.: 14/552,433

(22) Filed: Nov. 24, 2014

(65) Prior Publication Data

US 2016/0066854 A1    Mar. 10, 2016

Related U.S. Application Data

(60) Provisional application No. 62/046,441, filed on Sep. 5, 2014, provisional application No. 62/056,788, filed on Sep. 29, 2014.

(51) Int. Cl.
| | |
|---|---|
| *A61B 5/00* | (2006.01) |
| *H04B 5/00* | (2006.01) |
| *A61B 5/04* | (2006.01) |
| *A61B 5/01* | (2006.01) |

(52) U.S. Cl.
CPC ......... *A61B 5/6833* (2013.01); *H04B 5/0031* (2013.01); *H04B 5/0062* (2013.01); *A61B 5/0006* (2013.01); *A61B 5/0022* (2013.01); *A61B 5/01* (2013.01); *A61B 5/04* (2013.01)

(58) Field of Classification Search
CPC ... A61B 5/6833; H04B 5/0031; H04B 5/0062
USPC .......................................................... 600/391
See application file for complete search history.

(56) References Cited

U.S. PATENT DOCUMENTS

| | | |
|---|---|---|
| 2007/0270672 A1 | 11/2007 | Hayter |
| 2009/0171180 A1 | 7/2009 | Pering |
| 2012/0071742 A1* | 3/2012 | Medina ............... A61B 5/14552 600/344 |
| 2012/0242481 A1 | 9/2012 | Gernandt |

* cited by examiner

*Primary Examiner* — Nadia A Mahmood
(74) *Attorney, Agent, or Firm* — SV Patent Service

(57) ABSTRACT

An electronic sticker assembly includes a first electronic sticker comprising an upper surface, a lower surface, and a first group of conductive connection dots on the upper surface, a first adhesive layer on the first electronic sticker and comprising a first window. The first window is positioned to expose the first group of one or more conductive connection dots. A second electronic sticker on the first adhesive layer includes a lower surface and one or more second conductive connection dots on the lower surface. The first group of conductive connection dots on the upper surface of the first electronic sticker are in contact with the one or more second conductive connection dots on the lower surface of the second electronic sticker through the first window in the first adhesive layer.

14 Claims, 10 Drawing Sheets

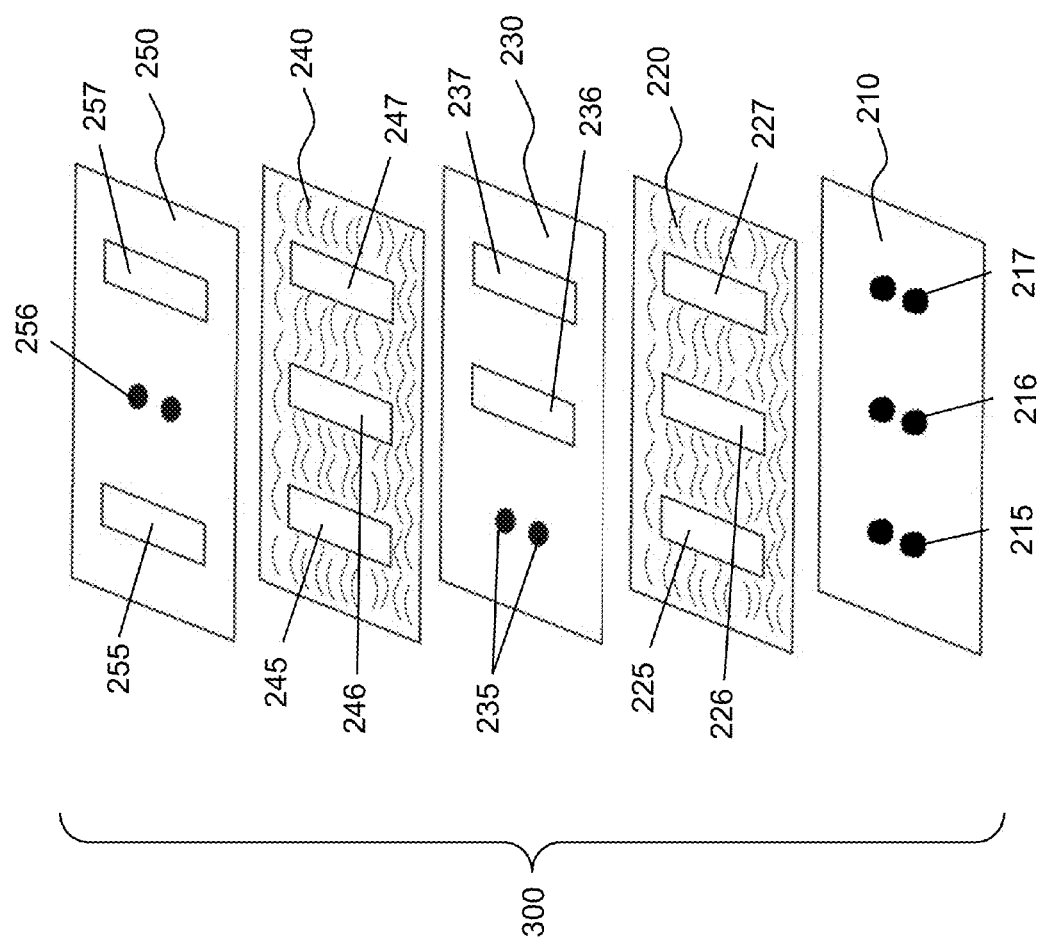

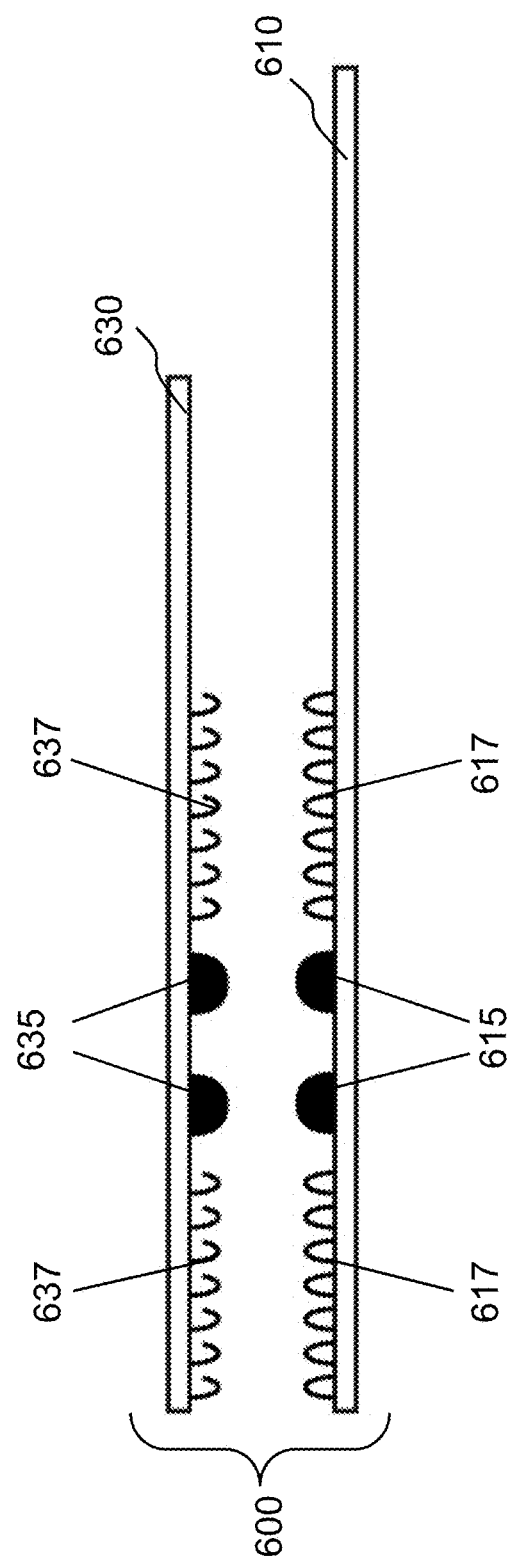

ELECTRONIC STICKERS WITH MODULAR STRUCTURES

BACKGROUND OF THE INVENTION

The present application relates to electronic devices, and in particular, to electronic stickers that can adhere to human skin or the surface of an object.

Wearable patches or tags can communicate with smart phones and other devices using WiFi, Bluetooth, or NFC technologies. Near Field Communication (NFC) is a wireless communication standard which enables two devices in a short range to establish a communication channel within a short period of time through radio waves in the 13.56 MHz frequency range. NFC can be a useful technology for data transfer between two devices in close proximity to one another. Because it needs the two devices to be in close proximity to one another (less than 10 cm), it is more secure than other wireless technologies like Bluetooth and Wi-Fi. Hence, it can be seen as an easy and secure tool for establishing quick two-way connections for data transfer. One of the two NFC devices can be a passive NFC tag that uses passive energy collected through active electromagnetic coupling from the reader devices, so it brings another benefit of no battery in its system that simplify the product design and make disposable product possible.

This communication standard is being increasingly adopted for use in wireless transactions, including money transfer, loyalty coupons, gift cards, transit passes, tickets, etc. Mobile handset manufacturing companies are increasingly integrating NFC hardware in their phones. For example, the 2014 CES badges employed NFC technology and have resulted in shorter lines, more badge functionality, and greater ease of use for attendees and exhibitors. NFC has also been increasingly used in the fields of medical devices, electronic health records, as well as wearable tagging devices.

In other scenarios, long communication distance is required, such as >10 meters. Without tapping the reader device in the close range NFC patch from time to time, data can be collected automatically and continuously with least operator interference. In such cases, Bluetooth and WiFi are a proper option with a 1.5V or 3V battery supply.

Wearable tag or patch is an electronic tag that can be worn by a user. Wearable patch is required to directly stay on user's skin and function for an extended period of time from hours to months. A wearable patch can contain a microelectronic system and can be accessed using NFC, Bluethooth, WiFi, or other wireless technologies. For example, an authentication wearable tag can be used to recognize a user's smart phone for authentication purpose. It can also be integrated with different sensors for other purposes such as vital signs monitoring, heartbeat, motion track, blood pressure, temperature measurements and ECG detection.

Despite initial development efforts, conventional wearable devices still face several drawbacks: they may not provide adequate comfort for users to wear them; they may not stay attached to user's body for the required length of time; they are usually not aesthetically appealing. Another drawback of conventional wearable patches is that the rigid polymer substrate does not allow much breathability to the skin. The build-up of sweat and moisture can cause discomfort and irritation to the skin, especially after wearing it for an extended period of time. In addition, their rigid substrates are very difficult to conform to curved surfaces, so some critical bio information needs to be collected with direct contact on skin without any air gap. For example, electrocardiography (usually called as ECG) picks up electrical impulses generated by the polarization and depolarization of cardiac tissue and translates into a waveform. The signals need to be detected by electrodes attached directly to the surface of the skin and recorded or displayed by a device external to the body. Air gap between the electrode and skin surface makes the measurement inaccurate. Moreover, conventional wearable devices are often not robust enough to sustain repeated elongations during the movements of the body that the wearable patches are attached to. Under stress, different layers in wearable patches can break or delaminate rendering the patches inoperable.

Wearable tags are a specific type of electronic stickers. In more general cases, electronic stickers can be attached not only to human bodies but also to other objects such as merchandized goods such as computers, smart phones, and clothes, packaging material and shipping boxes. Electronic stickers can communicate with smart phones or other devices wirelessly, through NFC, Bluetooth, WiFi, or other methods.

Electronic stickers can be used for tracking objects, for performing functions such as producing sound, light or vibrations, and so on. As the applications and human needs become more sophisticated and complex, there are a rapidly increasing number of tasks that electronic stickers are required to perform.

There is therefore a need for electronic stickers that can conveniently and economically measure different signals or perform different actuating functions.

SUMMARY OF THE INVENTION

The presently disclosure attempts to address the aforementioned limitations in conventional wearable tags and electronic stickers. The disclosed electronic stickers have modular structures that allow sticker structures with different functionalities to be flexibly combined or stacked and economically reused at locations as required by specification applications and needs. The applications for measuring signals such as temperature, heart beats, blood pressure, ECG, EEG, and EMG signals, motion signals, or for performing functions such as producing sound, light or vibrations, and so on.

Furthermore, the disclosed electronic stickers are highly compliant and flexible, while also being able to support the circuit, chips, and other electronic components, which make them to be suitable for being used as wearable tags. The disclosed electronic stickers can change their physical shape and dimension to relieve stresses such as repeated elongations, therefore increasing durability of the electronic stickers as well as provide comfort to the user. The disclosed electronic stickers can stay attached to skin for long period of time even enduring muscle movements underneath the skin to provide constant contact to the skin and comfort to the user.

Moreover, the disclosed electronic stickers are capable of measuring electrical signals in human body and are very stretchable, flexible, breathable, and comfortable to use.

In one general aspect, the present invention relates to an electronic sticker assembly that includes: a first electronic sticker comprising an upper surface, a lower surface, and a first group of one or more conductive connection dots on the upper surface, wherein the lower surface is configured to be adhered to a human skin or a surface of an object; a first adhesive layer on the first electronic sticker and comprising a first window, wherein the first window is positioned to expose the first group of one or more conductive connection dots; and a second electronic sticker on the first adhesive layer, wherein the second electronic sticker includes a lower surface and one or more second conductive connection dots on the lower surface, wherein the first group of one or more conductive connection dots on the upper surface of the first electronic sticker are configured to be in contact with the one or more second conductive connection dots on the lower surface of the second electronic sticker through the first window in the first adhesive layer.

Implementations of the system may include one or more of the following. At least some of the first group of one or more conductive connection dots and the one or more second conductive connection dots can be formed by an elastic or elastomer material embedded with a conductive material. The conductive connection dots can also be formed by a conductive mechanical component such as a spring or a snap-button set. At least one of the first electronic sticker and the second electronic sticker can include a semiconductor chip and a conductive circuit. The semiconductor chip and the conductive circuit can wirelessly communicate with the external device based on near field communication (NFC), Wi-Fi, Bluetooth, or RFID wireless communication standard. The conductive circuit can include an antenna circuit configured to receive or transmit wireless signals in communications with the external device. At least one of the first electronic sticker and the second electronic sticker can include at least one sensor or one actuator. The sensor can include an electrode configured to be in contact with a user's body and to pick up electric signals from the user's body. The first electronic sticker and the second electronic sticker can each include at least one sensor or one actuator, wherein the sensor or the actuator in one of the first electronic sticker and the second electronic sticker is configured to dynamically change its function in response to a measured signal or a control signal of the other one of the first electronic sticker and the second electronic sticker. At least one of the first electronic sticker and the second electronic sticker can include an elastic layer and a support substrate, wherein the support substrate is configured to support at least one sensor or one actuator. The support substrate can have a Young's Modulus higher than 0.5 Gpa. The elastic layer can have a Young's Modulus lower than 0.3 Gpa. The first electronic sticker further can include a second group of one or more conductive connection dots on the upper surface, wherein the first adhesive layer can include a second window, wherein the second electronic sticker can include a third window, the electronic sticker assembly can further include: a second adhesive layer on the second electronic sticker and comprising a fourth window, wherein the second window, the third window, and the fourth window are positioned to expose the second group of one or more conductive connection dots; and a third electronic sticker on the second adhesive layer, wherein the second electronic sticker includes a lower surface and one or more third conductive connection dots on the lower surface, wherein the second group of one or more conductive connection dots on the upper surface of the first electronic sticker are configured to be in contact with the one or more third conductive connection dots on the lower surface of the second electronic sticker through the second window, the third window, and the fourth window. The electronic sticker assembly can further include a fourth electronic sticker over the first electronic sticker and on the side of the second electronic sticker, wherein the first electronic sticker comprises a third group of one or more conductive connection dots on the upper surface, wherein the fourth electronic sticker includes a lower surface and one or more fourth conductive connection dots on the lower surface, wherein the one or more fourth conductive connection dots are configured to be electrically connected with the third group of one or more conductive connection dots. The electronic sticker assembly can further include a third adhesive layer between the first electronic sticker and the fourth electronic sticker layer.

In another general aspect, the present invention relates to an electronic sticker assembly that includes a first electronic sticker comprising an upper surface, a lower surface, and one or more first conductive connection dots on the upper surface, wherein the lower surface is configured to be adhered to a human skin or a surface of an object; a second electronic sticker over the first electronic sticker, wherein the second electronic sticker includes a lower surface and one or more second conductive connection dots on the lower surface; and magnetic materials on the upper surface of the first electronic sticker and the lower surface of the second electronic sticker, wherein the magnetic materials are configured to attract each other to cause the one or more first conductive connection dots to come into contact with the one or more second conductive connection dots.

Implementations of the system may include one or more of the following. The magnetic materials can include a permanent magnetic material on at least one of the upper surface of the first electronic sticker or the lower surface of the second electronic sticker. At least some of the one or more first conductive connection dots and the one or more second conductive connection dots are formed by an elastic or elastomer material embedded with a conductive material. The conductive connection dots can also be formed by a conductive mechanical component such as a spring or a snap-button set. When the first electronic sticker is bonded with the main electronic sticker, the conductive connection dots on the first modular electronic sticker have secure electric contacts with the conductive connection dots on a main electronic sticker. The electronic sticker assembly can further include a third electronic sticker over the first electronic sticker, wherein the third electronic sticker includes a lower surface and one or more third conductive connection dots on the lower surface, wherein the third electronic sticker and the first electronic sticker are electrically connected and are physically bonded together by a magnetic force.

In another general aspect, the present invention relates to an electronic sticker assembly that includes a first electronic sticker comprising an upper surface, a lower surface, and one or more first conductive connection dots on the upper surface, wherein the lower surface is configured to be adhered to a human skin or a surface of an object; a second electronic sticker over the first electronic sticker, wherein the second electronic sticker includes a lower surface and one or more second conductive connection dots on the lower surface; and a pair of hook and loop respectively fixed on the upper surface of the first electronic sticker and the lower surface of the second electronic sticker, wherein the pair of hook and loop is configured to pull the first electronic sticker and the second electronic sticker to cause the one or more first conductive connection dots to come into contact with the one or more second conductive connection dots.

Implementations of the system may include one or more of the following. At least some of the one or more first conductive connection dots and the one or more second conductive connection dots can be formed by a matrix of elastic or elastomer material embedded with a conductive material. The conductive connection dots can also be formed by an elastic mechanical component such as a spring or a snap-button set. When the first electronic sticker is bonded with the main electronic sticker, the conductive connection dots on the first modular electronic sticker have secure electric contacts with the conductive connection dots on a main electronic sticker. The electronic sticker assembly can further include a third electronic sticker over the first electronic sticker, wherein the third electronic sticker includes a lower surface and one or more third conductive connection dots on the lower surface, wherein the third electronic sticker and the first electronic sticker are electrically connected and are physically bonded together by a hook-and-loop mechanism.

These and other aspects, their implementations and other features are described in detail in the drawings, the description and the claims.

BRIEF DESCRIPTION OF THE DRAWINGS

FIG. 3A is an exploded perspective view of an electronic sticker assembly comprising two modular electronic stickers stacked on a main electronic sticker in accordance with some embodiments of the present invention.

FIG. 6 is an exploded cross-sectional view of two electronic stickers that connected by hook-and-loop mechanism in accordance with some embodiments of the present invention.

DETAILED DESCRIPTION OF THE INVENTION

Figure 1:
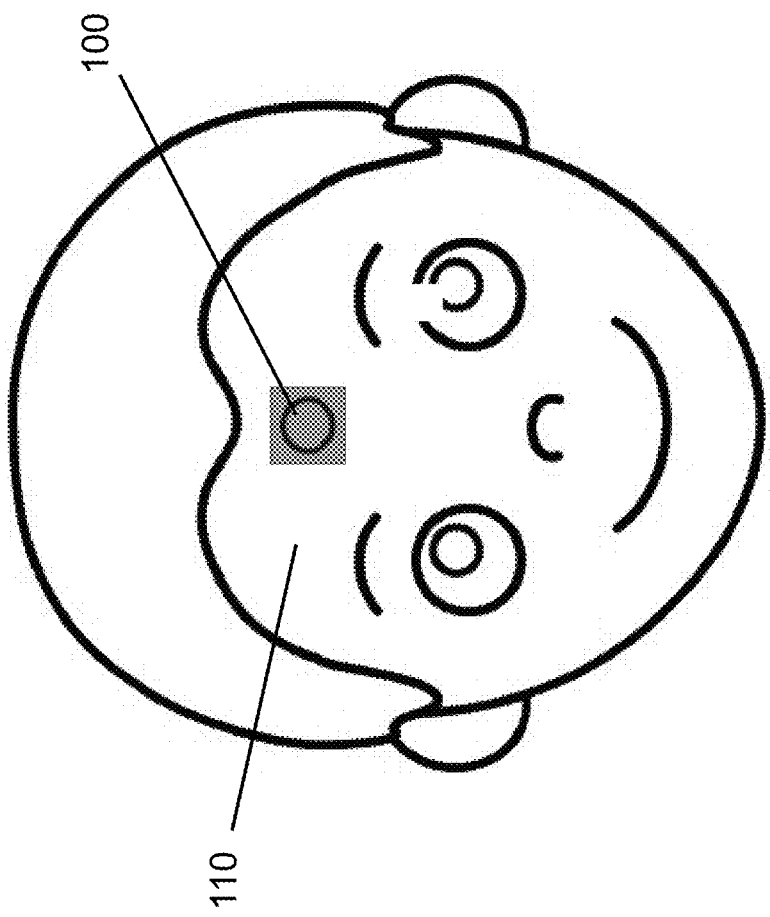
FIG. 1 illustrates an electronic sticker attached to a user's skin.

The presently disclosure aims to provide electronic stickers with a wide range of sensing and/or actuating functions. FIG. 1 shows an exemplified electronic sticker 100 placed on and adheres to a person's skin 110 on his or her body such as forehead, hand, wrist, arm, shoulder, breast, waist, leg, foot, etc. The compliant electronic sticker 100 can be used for measuring signals such as temperature, heart beats, blood pressure, EEG signals, motion signals, or for performing functions such as producing sound, light or vibrations, and so on. The electronic sticker 100 can also be attached to an object for tracking, or measuring or producing signals.

Figure 2A:
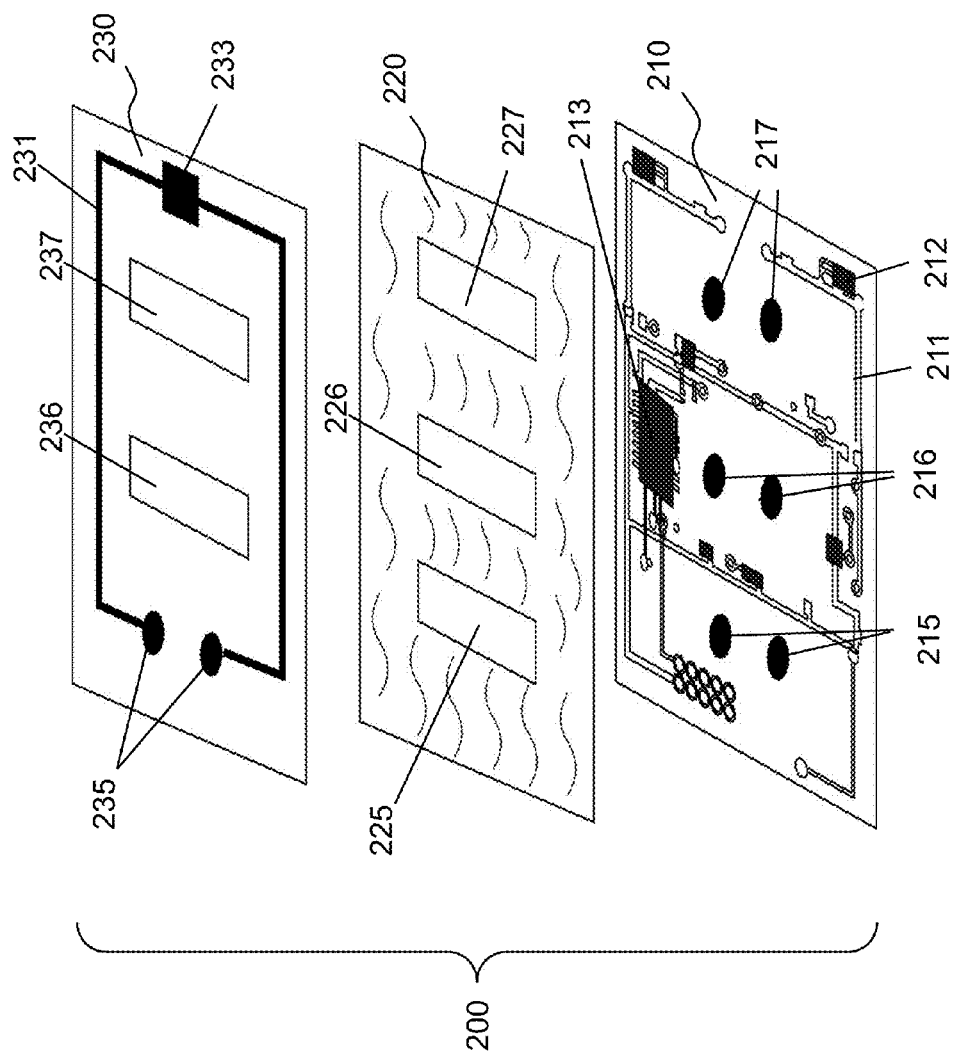
FIG. 2A is an exploded perspective view of an electronic sticker assembly comprising a modular electronic sticker stacked on a main electronic sticker in accordance with some embodiments of the present invention.
Figure 2B:
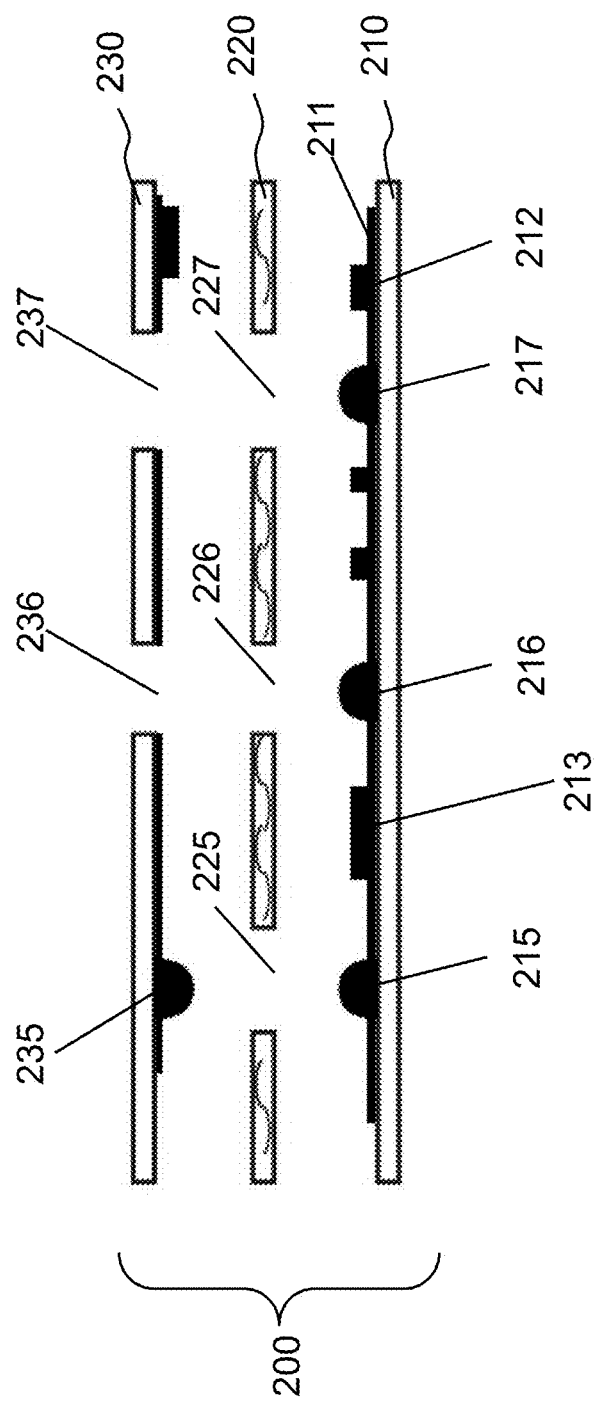
FIG. 2B is an exploded cross-sectional view of the modular electronic sticker and the main electronic sticker in FIG. 2A.
Figure 2C:
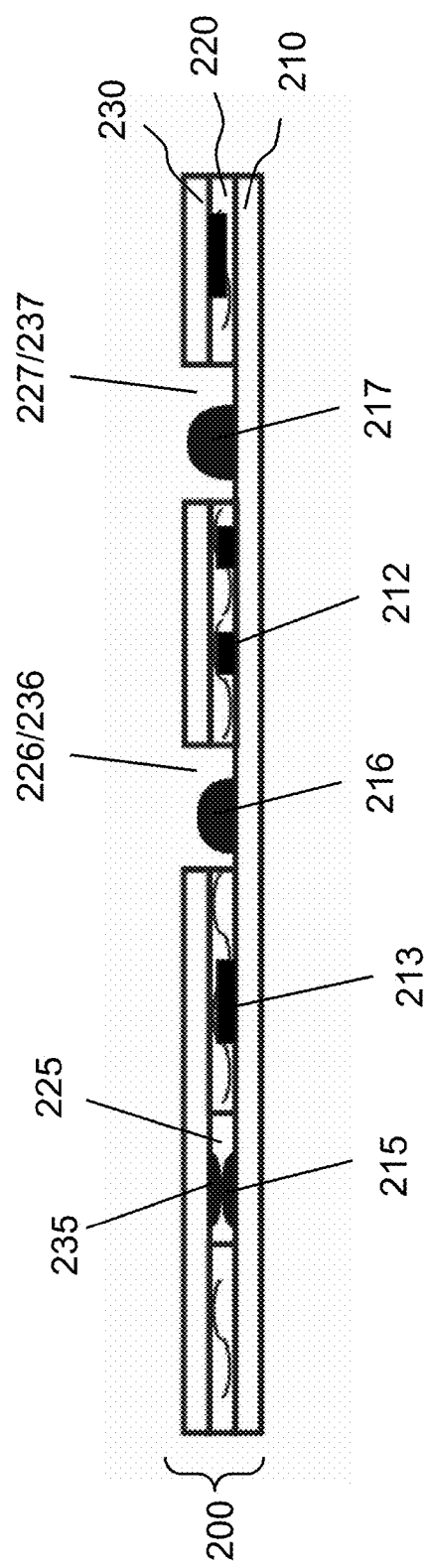
FIG. 2C is a cross-sectional view of an electronic sticker assembly comprising the modular electronic sticker and the main electronic sticker in FIGS. 2A and 2B.

Referring to FIGS. 2A-2C, an electronic sticker assembly 200 includes a main electronic sticker 210 that includes a plurality of conductive connection dots 215, 216, 217 on the upper surface of the main electronic sticker 210. The conductive connection dots 215, 216, 217 can be arranged in separate groups, which as described below are configured to connect to different electronic stickers. The connection dots 215, 216, 217 can be formed by a matrix of an elastic or elastomer material such as silicone or polyurethane embedded with a conductive material such as silver particles or silver flakes. The connection dots can also be conductive mechanical components as mentioned above.

The main electronic sticker 210 can include a circuit 211, electronic components 212, and semiconductor chip(s) 213 for performing one or more functions. The main electronic sticker 210 can be applied with an adhesive on its lower surface to enable it to be adhered to a human skin or the surface of an object.

The electronic sticker assembly 200 also includes a modular electronic sticker 230 on an adhesive layer 220, which are stacked on the main electronic sticker 210. The modular electronic sticker 230 can include a circuit 231, a semiconductor chip 233 and other electronic components. The adhesive layer 220 includes a plurality of windows 225, 226, 227 positioned to respectively expose the connection dots 215, 216, 217. The adhesive layer 220 can be a pressure sensitive adhesive or a repositionable type adhesive, which can be removed easily without damaging the main electronic sticker. The modular electronic sticker 230 includes conductive connection dots 235 on a lower surface of the modular electronic sticker 230. The connection dots 235 are positioned to come in contact with the connection dots 215 on the main electronic sticker 210 through the window 225 in the adhesive layer 220. The modular electronic sticker 230 can include windows 236, 237, which, in combination with windows 226, 227 in the adhesive layer 220, can respectively expose the connection dots 216, 217 on the main electronic sticker 210.

The electronic communication between the modular electronic sticker 230 and the main electronic sticker 210 allow them to share communication and control functions in the electronic sticker assembly 200. For example, if the main electronic sticker 210 includes functions of wireless communications with external devices, the control and measurement information associated with the modular electronic sticker 230 can be communicated with the external device via the main electronic sticker 210. Functions of main electronic sticker 210 can be extended through electronic connection with one or multiple modular electronic sticker or stickers in a flexible way. The main electronic sticker 210 works as a skeleton with a set of modular component stickers such as 230 holding to it. Functions of the whole electronic sticker 200 can be customized through integration of single or multiple modular stickers 210.

In some embodiments, the electronic sticker assembly 200 can include certain "local intelligence" that enable the modular electronic sticker 230 and the main electronic sticker 210 to dynamically change how they perform their respective functions. In other words, the sensor and/or the actuator in one of the electronic stickers 210, 230 can dynamically change its function in response to a measured signal or a control signal of the other one of the electronic stickers 210, 230. For example, the main electronic sticker 210 can measure human organ electrical activities such as ECG, EEG, EMG while the modular electronic sticker 230 can measure heart beat or/and can produce light or acoustic signals. The main electronic sticker 210 can be pre-stored or programmed with such logic and intelligence which can send control signal to the modular electronic sticker 230 in response to the electrical signals it has measured from the user's body. In one application, EEG and heart beats can be simultaneously measured to allow them to be corroborated for analysis. In another application, when an abnormal EEG signal is detected, the main electronic sticker 210 can send a control signal to the modular electronic sticker 230 to cause it to emit light or sound for warning signals.

In another example, the modular electronic sticker 250 can include a temperature sensor which output an electrical signal representing the detected ambient temperature, while the bottom main electronic sticker 210 measure the skin surface temperature with direct contact on skin surface. The electrical signal of ambient temperature reading from modular electronic sticker 230 is transmitted to the main electronic sticker 210 via the connection dots 236 and 215 that are in contact with each other. The ambient temperature reading from module electronic sticker 250 is important index to correct to the skin surface temperature reading collected by bottom main electronic sticker 210. It can be used in the scenario in which body temperature needs to be very precisely monitored, such as for women to monitor body temperature cycle of period to predict the best time for conceiving pregnancy.

The main electronic sticker 210 and the modular electronic sticker 230 can each include one or more layers. For example, they can include one or more elastic layers and a support substrate. The elastic layers can be made of a viscoelastic polymeric material having low Young's modulus and high failure strain. In some embodiments, an elastic layer can have Young's Modulus <0.3 Gpa. In some cases, an elastic layer can have Young's Modulus <0.1 Gpa to provide enhanced flexibility and tackability. Materials suitable for the elastic layer include elastomers, viscoelastic polymers, such as silicone, and medical grade polyurethane that is a transparent medical dressing used to cover and protect wounds with breathability and conformation to skin. The support substrate, on the other hand, is rigid enough to provide support to a circuit 211 such as an antenna circuit, electronic components 212 such as resistors, capacitors, sensors, actuators, and chemical delivery devices, etc., and a semiconductor chip 213. Other electronic components can include capacitors, inductors, resistors, metal pads, diodes, transistors, and amplifiers. In some embodiments, the support substrate can have Young's Modulus larger than 0.5 Gpa, such as in a range between 1.0-10 Gpa. Examples of materials suitable for the substrate include Polyimide, polyester, Aramid, Composite, Glass epoxy, and Polyethylene naphalate. Importantly, the support substrate is structured to provide stretchability to the main and modular stickers. The support substrate can include one or more openings, which makes the electronic stickers shearable and stretchable when they are is stretched or elongated. By strategically forming openings in the support substrate, the effective elasticity of the support substrate is increased significantly above the intrinsic elasticity the material in the support substrate (the effective elastic constant is decreased).

Details about stretchable and shearable multi-layer wearable tags or patches as specific examples of the disclosed electronic stickers are disclosed in commonly assigned pending U.S. patent application Ser. No. 14/454,457, titled "Stretchable multi-layer wearable tag capable of wireless communications", filed on Aug. 7, 2014, U.S. patent application Ser. No. 14/491,665, titled "Highly compliant wearable wireless patch having stress-relief capability", filed on Sep. 19, 2014, and U.S. patent application Ser. No. 14/520,674, titled "Compliant wearable patch capable of measuring electrical signals", filed on Oct. 10, 2014. The disclosures of these applications are incorporated herein by reference.

Figure 3B:
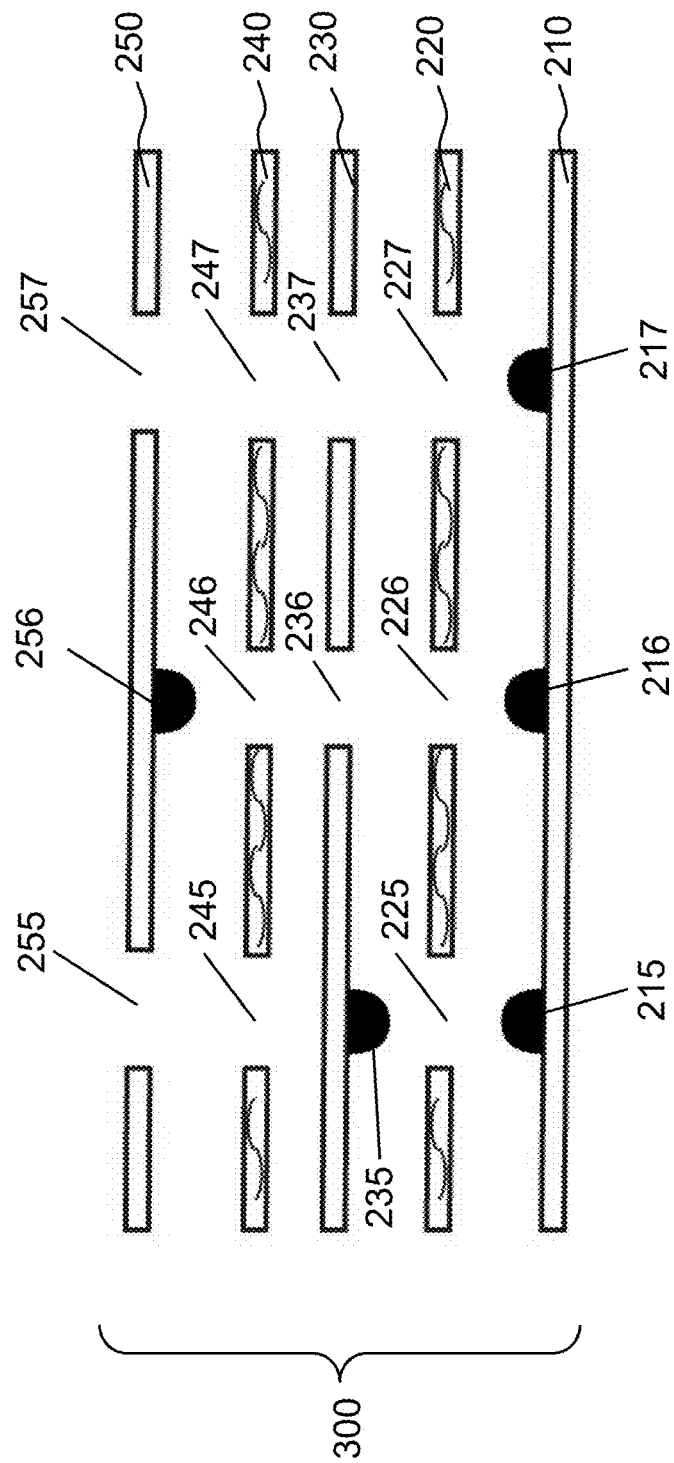
FIG. 3B is an exploded cross-sectional view of the two modular electronic stickers and the main electronic sticker in FIG. 3A.
Figure 3C:
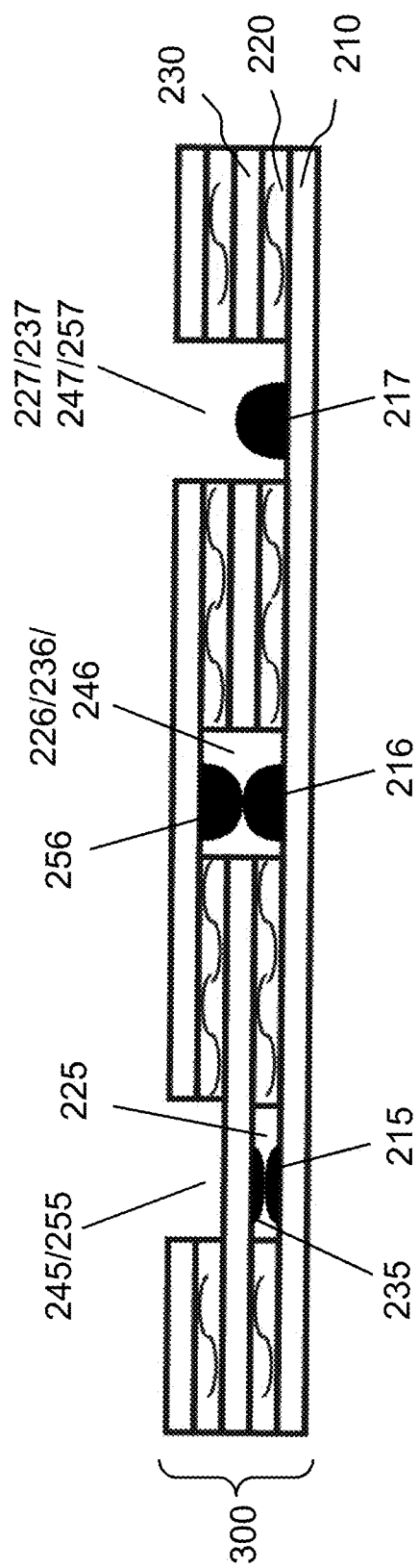
FIG. 3C is a cross-sectional view of an electronic sticker assembly comprising the two modular electronic stickers and the main electronic sticker in FIGS. 3A and 3B.

In some embodiments, three electronic stickers can be stacked to achieve a wider range of functions. Referring to FIGS. 3A-3C, an electronic sticker assembly 300 includes a main electronic sticker 210, and two modular electronic stickers 230, 250 in a sequentially stacked structure. Similar to the electronic sticker assembly 200 described above, the main electronic sticker 210 and the modular electronic sticker 230 are stacked with an adhesive layer 220 in between.

The main electronic sticker 210 can include a layer of adhesive on its lower surface. The adhesive layer can be pressure sensitive, which allows the main electronic sticker 210 tightly adhere to human skin under pressure, applied for example by a thumb. For instance, the adhesive layer can be made of a medical pressure sensitive adhesive. An example of such adhesive is medical grade tackified Hypoallergenic Pressure Sensitive Adhesive.

The main electronic sticker 210 can include a circuit such as an antenna circuit, electronic components, and semiconductor chip(s), which are not shown for clarity reason, for performing one or more functions. The main electronic sticker 210 can be applied with an adhesive on its lower surface to enable it to be adhered to a human skin or the surface of an object. The main electronic sticker 210 and the modular electronic sticker 230 can electronically communicate with each other via the conductive connection dots 215 and the conductive connection dots 235 which are in contact through the window 225 in the adhesive layer.

As discussed above, the windows 226, 227 in the adhesive layer 220 and the windows 236, 237 in the modular electronic sticker 230 allow the conductive connection dots 216, 217 to be connected to the second modular electronic sticker 250. The electronic sticker assembly 200 further includes an adhesive layer 240 on the lower surface of the modular electronic sticker 250. The adhesive layer 240 includes a plurality of windows 245, 246, 247 positioned respectively in registration with the connection dots 215/235, 216, 217.

A modular electronic sticker 250 is placed on the adhesive layer 240. The modular electronic sticker 230 includes, on its lower surface, conductive connection dots 256 positioned to be in contact with the connection dots 216 on the main electronic sticker 210 through the window 226, 236, 246 in the adhesive layers and the modular electronic sticker 230. The modular electronic sticker 250 can include windows 255, 257, which allow additional electronic stickers to be stacked and communicate with the connection dots 235, 217 on the modular electronic sticker 230 and the main electronic sticker 210.

Similar to the description above relating to the electronic sticker assembly 200, the main electronic sticker 310 and the modular electronic stickers 330, 350 can each include one or more layers such as one or more elastic layers and a support substrate that hold the electronic components.

In some embodiments, at least one of the main electronic sticker 210 and the modular electronic stickers 230, 250 is configured to wirelessly communicate with external devices, based on wireless communication standards such as NFC standard, RFID, Wi-Fi, or Bluetooth. The main electronic sticker 210 and/or the two modular electronic stickers 230, 250 can include a support substrate, and one or multiple semiconductor chips, a circuit, and an antenna circuit formed on or in the support substrate. Examples of external devices include smart phones, computers, mobile payment devices, scanners and readers (e.g. RFID readers), medical devices, security systems, personal identification systems, etc. The antenna circuit can be compatible for NFC communications in a frequency range near 13.56 MHz, as described above, as well as UHF RFID at about 915 MHz, Bluetooth in 2.4 GHz or 5 GHz frequency ranges, and other types of wireless communications.

Details about wireless communications between stretchable and shearable multi-layer wearable tags or patches and external devices are disclosed in commonly assigned pending U.S. patent application Ser. No. 14/454,457, titled "Stretchable multi-layer wearable tag capable of wireless communications", filed on Aug. 7, 2014, U.S. patent application Ser. No. 14/491,665, titled "Highly compliant wearable wireless patch having stress-relief capability", filed on Sep. 19, 2014, and U.S. patent application Ser. No. 14/520,674, titled "Compliant wearable patch capable of measuring electrical signals", filed on Oct. 10, 2014. The disclosures of these applications are compatible with the presently disclosed electronic stickers, and are incorporated herein by reference.

For example, the main electronic sticker 210 can include necessary semiconductor chip, circuit, and optionally an antenna circuit for wireless communications. In one application, the main electronic sticker 210 can also include an electrode layer that is configured to be in contact with a user's skin for measuring human organ electrical activities such as ECG, EEG, EMG, etc. Such electrical signals can be transmitted to an external device by the main electronic sticker 210. Details about multi-layer wearable tags or patches that are capable of measuring electric signals in human bodies, which compatible with the disclosed electronic stickers, are disclosed in commonly assigned pending U.S. patent application Ser. No. 14/520,674, titled "Compliant wearable patch capable of measuring electrical signals", filed on Oct. 22, 2014, the disclosure of which is incorporated herein by reference.

In another example, the modular electronic sticker 250 can for example include sensors configured for measuring a user's heart beats. The electrical signal output from the sensors is transmitted to the main electronic sticker 210 via the connection dots 256 and 216 which are in contact with each other, which is in turn wirelessly transmitted to an external device. Similarly, additional modular electronic stickers can be added to the electronic sticker assembly to perform additional functions.

In some embodiments, the modular electronic stickers can be disposable components while the main electronic sticker is used on a long term base. The main electronic sticker can include more complex and expensive components for functions such as wireless communications and certain actuator functions. The modular electronic stickers can be changed when different applications are required.

In some embodiments, one modular electronic sticker can be a battery module, which can supply electric power to the main electronic sticker and other modular electronic stickers. After the power is used up in the battery, that modular electronic sticker can be removed and charged separately by a charging device; it can also be replaced by a new battery module.

In some embodiments, the main sticker can perform mainly adhesive functions. The main sticker can have bonding to surface function on both sides, which bind it to a user's skin and other modular electronic stickers. After a period of use when the function is not temporarily required, the sticker assembly can be removed from user's skin; the main sticker is discarded. Other modular electronic stickers stacked on top can be stored and reused later. If the main sticker becomes dirty or has lost adhesive power, it can be replaced by a new main sticker for a new period of wearing and measurement. This way, modular electronic stickers can be used for days and weeks without losing bonding to skin and incurring cost of new stickers. Sometimes, the top module sticker can be decoration layer with graphic patterns put on bottom stickers. The graphic pattern can be customized to fit in different cosmetic preference.

Figure 4:
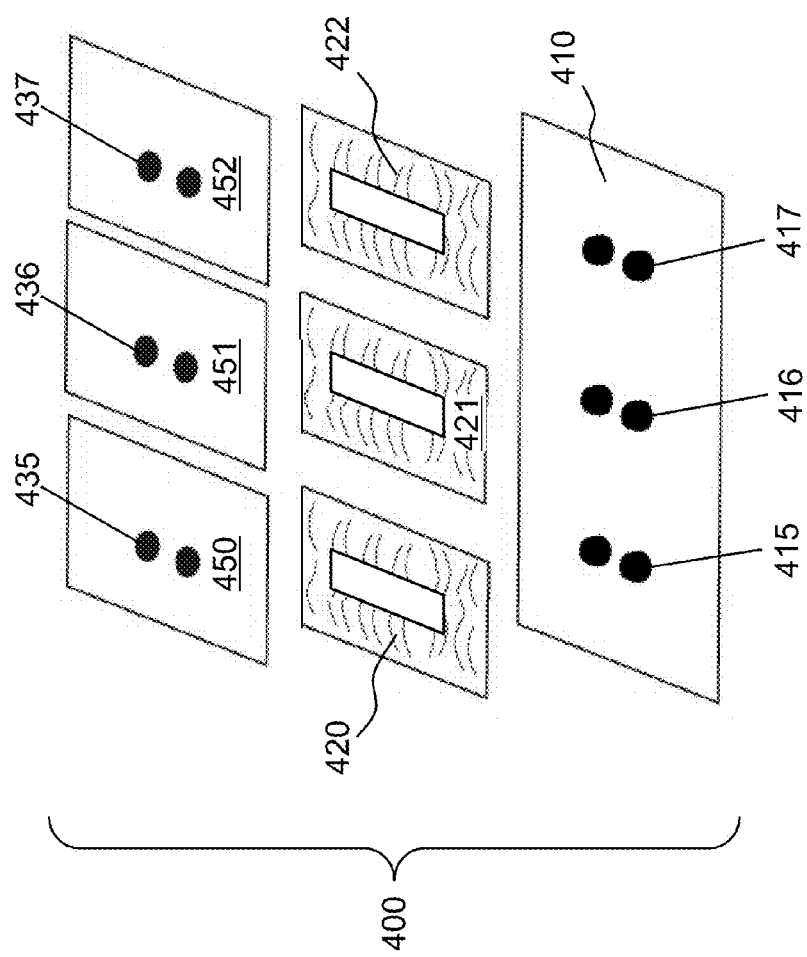
FIG. 4 is an exploded perspective view of an electronic sticker assembly comprising multiple modular electronic stickers positioned in parallel on a main electronic sticker in accordance with some embodiments of the present invention.

The presently disclosed electronic sticker assembly can include multiple modular electronics stickers positioned side by side on a main electronic sticker. Referring to FIG. 4, an electronic sticker assembly 400 includes a main electronic sticker 410, and three modular electronic stickers 450-452 that are stacked side by side on the main electronic sticker 410. Similar to the electronic sticker assemblies 200, 300 (FIGS. 2A-3C) described above, the modular electronic sticker 450-452 are stacked on the main electronic sticker 410 with adhesive layers 420-422 respectively sandwiched in between. The main electronic sticker 410 and the modular electronic stickers 450-452 can include circuits such as an antenna circuit, electronic components, and semiconductor chip(s), which are not shown for clarity reason, for performing one or more functions.

The main electronic sticker 410 can include a layer of adhesive on its lower surface. The adhesive layer can be pressure sensitive, which allows the main electronic sticker 410 tightly adhere to human skin under pressure, applied for example by a thumb. For instance, the adhesive layer can be made of a medical pressure sensitive adhesive. An example of such adhesive is medical grade tackified Hypoallergenic Pressure Sensitive Adhesive.

The main electronic sticker 410 can include a circuit such as an antenna circuit, electronic components, and semiconductor chip(s) (not shown for clarity reason) for performing one or more functions. The main electronic sticker 410 and the modular electronic stickers 450-452 can electronically communicate with each other via the conductive connection dots 415-417 and the conductive connection dots 435-437 respectively through the windows in the adhesive layers 420-422.

Figure 5:
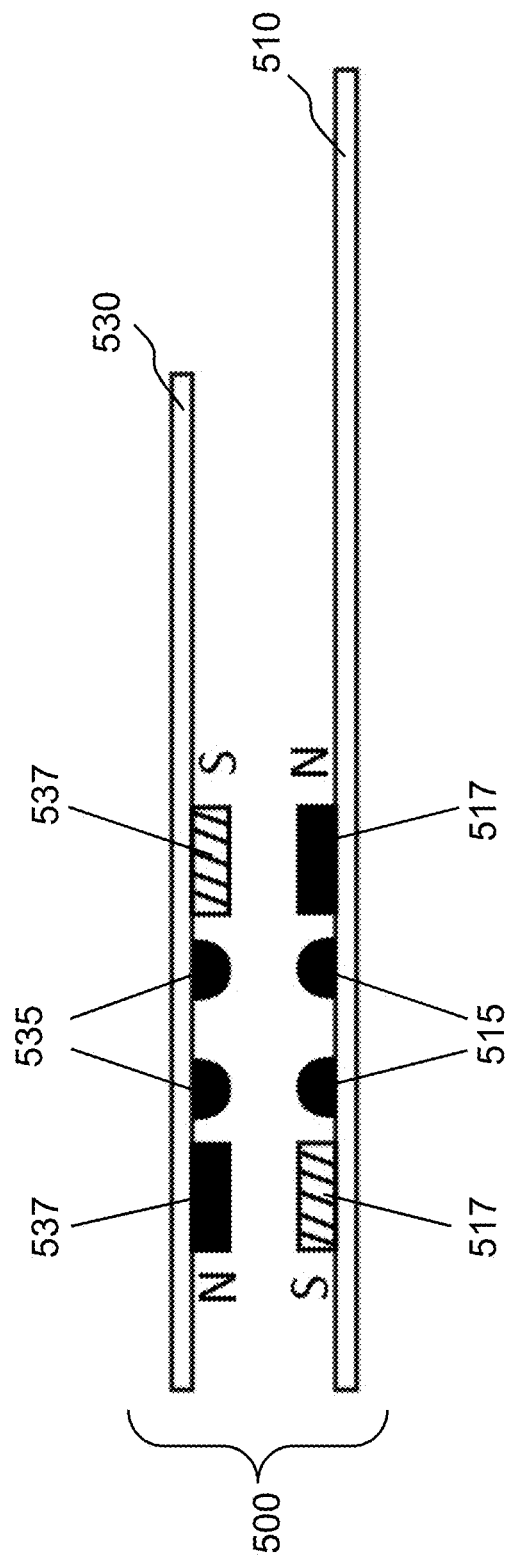
FIG. 5 is an exploded cross-sectional view of two electronic stickers that connected by magnetic force in accordance with some embodiments of the present invention.

In some embodiments, the main and the modular electronic stickers can be bound to each other by using different mechanisms from adhesive layers. In some embodiments, referring to FIG. 5, an electronic sticker assembly 500 includes a main electronic sticker 510 and a modular electronic sticker 530, which respectively include conductive connection dots 515, 535. The main electronic sticker 510 and the modular electronic sticker 530 can include a circuit such as an antenna circuit, electronic components, and semiconductor chip(s), which are not shown for clarity reason, for performing one or more functions. The connection dots 515, 535 can be formed by a matrix of elastic or elastomer material such as silicone or polyurethane embedded with a conductive material such as silver particles or silver flakes. The connection dots can also be conductive mechanical components such as a spring or a snap-button set. Moreover, the main electronic sticker 510 and the modular electronic sticker 530 also respectively include magnets 517 and 537 which are attracted to each other and can bond the main electronic sticker 510 and the modular electronic sticker 530 together. The magnetic forces pull the elastic connection dots 515, 535 together to increase contact area and to form a closed conductive circuit. The magnets 517 and 537 can have opposing magnetic polarities that attract each other across the electronic stickers 510, 530. In another implementation, a permanent magnet can be placed on one of the electronic stickers while a paramagnetic material is placed at an opposing position on another electronic sticker. The permanent magnet is attracted to the paramagnetic material by inducing an opposite magnet field in the paramagnetic material. Multiple modular stickers can be stacked with the stacks of magnet buttons in a similar way.

In some embodiments, referring to FIG. 6, an electronic sticker assembly 600 includes a main electronic sticker 610 and a modular electronic sticker 630, which respectively include conductive connection dots 615, 635. The main electronic sticker 610 and the modular electronic sticker 630 can include a circuit such as an antenna circuit, electronic components, and semiconductor chip(s), which are not shown for clarity reason, for performing one or more functions. The main electronic sticker 610 and the modular electronic sticker 630 also respectively include loops 617 and hooks 637 respectively fixed on the upper surface of the main electronic sticker 610 and the lower surface of the modular electronic sticker 630. The loops 617 and the hooks 637 can be hooked to bond the main electronic sticker 610 and the modular electronic sticker 630 together. The elastic connection dots 615, 635 are pulled together to form a closed conductive circuit. The loops 617 and the hooks 637 are positioned in pairs in any sequence between the main electronic sticker 610 and the modular electronic sticker 630.

The magnetic and hook-loop mechanisms can be incorporated into the electronic sticker assemblies 200 and 300, described above in FIGS. 2A-3C, to replace the adhesive layers between the electronic stickers to bind the electronic stickers together.

In some embodiments, multiple modular electronic stickers can be positioned side by side on a main electronic sticker and connected to the main electronic sticker using the magnetic and hook-loop mechanisms. In the electronic sticker assembly 500 (FIG. 5), a second modular electronic sticker can be positioned on the main electronic sticker 510 by the side of the modular electronic sticker 530. The second modular electronic sticker can be physically and electrically connected to the main electronic sticker 510 with similar mechanisms as those between the modular electronic sticker 530 and the main electronic sticker 510.

Similarly, in the electronic sticker assembly 600 (FIG. 6), a second modular electronic sticker can be positioned on the main electronic sticker 610 by the side of the modular electronic sticker 630. The second modular electronic sticker can be physically and electrically connected to the main electronic sticker 610 with similar mechanisms as those between the modular electronic sticker 630 and the main electronic sticker 610.

An advantage of the disclosed electronic stickers is that they allow electronic stickers of different sensing and actuation functions to be flexibly combined, which allows a broader range of functions. Moreover, the structure of each modular electronic sticker can be made simpler because they are not required to be loaded with too many functions. Modular electronic stickers can be reused, which decreases waste and cost.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Only a few examples and implementations are described. Other implementations, variations, modifications and enhancements to the described examples and implementations may be made without deviating from the spirit of the present invention. For example, the usages of the disclosed electronic stickers are not limited by the examples given above; they can be applicable to many other fields. The materials suitable for the different layers of the electronic stickers are also not limited by the examples provided. The layouts and forms of the elastic layer, the compliant strap layers, the breathing openings, the decorative pattern, the semiconductor chip, the antenna, the metal pads, and the connection leads can have other configurations without deviating from the present invention.

What is claimed is:

1. An electronic sticker assembly, comprising:
a first electronic sticker comprising an upper surface, a lower surface, and a first group of one or more conductive connection dots on the upper surface, wherein the lower surface is configured to be adhered to a human skin or a surface of an object;
a first adhesive layer on the first electronic sticker and comprising a first window, wherein the first window is positioned to expose the first group of one or more conductive connection dots; and
a second electronic sticker on the first adhesive layer, wherein the second electronic sticker includes a lower surface and one or more second conductive connection dots on the lower surface, wherein the first group of one or more conductive connection dots on the upper surface of the first electronic sticker are configured to be in contact with the one or more second conductive connection dots on the lower surface of the second electronic sticker through the first window in the first adhesive layer.

2. The electronic sticker assembly of claim 1, wherein at least some of the first group of one or more conductive connection dots and the one or more second conductive connection dots are formed by a conductive material or an elastic or elastomer material embedded with a conductive material.

3. The electronic sticker assembly of claim 1, wherein at least one of the first electronic sticker and the second electronic sticker includes a semiconductor chip and a conductive circuit.

4. The electronic sticker assembly of claim 3, wherein the semiconductor chip and the conductive circuit are configured to wirelessly communicate with the external device based on near field communication (NFC), Wi-Fi, Bluetooth, or RFID wireless communication standard.

5. The electronic sticker assembly of claim 4, wherein the conductive circuit includes an antenna circuit configured to receive or transmit wireless signals in communications with the external device.

6. The electronic sticker assembly of claim 1, wherein at least one of the first electronic sticker and the second electronic sticker includes at least one sensor or one actuator.

7. The electronic sticker assembly of claim 6, wherein the sensor includes an electrode configured to be in contact with a user's body and to pick up electric signals from the user's body.

8. The electronic sticker assembly of claim 1, wherein the first electronic sticker and the second electronic sticker each includes at least one sensor or one actuator, wherein the sensor or the actuator in one of the first electronic sticker and the second electronic sticker is configured to dynamically change its function in response to a measured signal or a control signal of the other one of the first electronic sticker and the second electronic sticker.

9. The electronic sticker assembly of claim 1, wherein at least one of the first electronic sticker and the second electronic sticker includes an elastic layer and a support substrate, wherein the support substrate is configured to support at least one sensor or one actuator.

10. An electronic sticker assembly, comprising:
a first electronic sticker comprising an upper surface, a lower surface, and a first group of one or more conductive connection dots on the upper surface, wherein the lower surface is configured to be adhered to a human skin or a surface of an object;
a first adhesive layer on the first electronic sticker and comprising a first window, wherein the first window is positioned to expose the first group of one or more conductive connection dots; and
a second electronic sticker on the first adhesive layer, wherein the second electronic sticker includes a lower surface and one or more second conductive connection dots on the lower surface, wherein the first group of one or more conductive connection dots on the upper surface of the first electronic sticker are configured to be in contact with the one or more second conductive connection dots on the lower surface of the second electronic sticker through the first window in the first adhesive layer,
wherein at least one of the first electronic sticker and the second electronic sticker includes a support substrate, wherein the support substrate is configured to support at least one sensor or one actuator, wherein the support substrate has a Young's Modulus higher than 0.5 Gpa.

11. An electronic sticker assembly, comprising:
a first electronic sticker comprising an upper surface, a lower surface, and a first group of one or more conductive connection dots on the upper surface, wherein the lower surface is configured to be adhered to a human skin or a surface of an object;
a first adhesive layer on the first electronic sticker and comprising a first window, wherein the first window is positioned to expose the first group of one or more conductive connection dots; and
a second electronic sticker on the first adhesive layer, wherein the second electronic sticker includes a lower surface and one or more second conductive connection dots on the lower surface, wherein the first group of one or more conductive connection dots on the upper surface of the first electronic sticker are configured to be in contact with the one or more second conductive connection dots on the lower surface of the second electronic sticker through the first window in the first adhesive layer,
wherein at least one of the first electronic sticker and the second electronic sticker includes an elastic layer, wherein the elastic layer has a Young's Modulus lower than 0.3 Gpa.

12. The electronic sticker assembly of claim 11, wherein the first electronic sticker comprises a second group of one or more conductive connection dots on the upper surface, wherein the first adhesive layer comprises a second window, wherein the second electronic sticker comprises a third window, the electronic sticker assembly further comprising:
a second adhesive layer on the second electronic sticker and comprising a fourth window, wherein the second window, the third window, and the fourth window are positioned to expose the second group of one or more conductive connection dots; and
a third electronic sticker on the second adhesive layer, wherein the second electronic sticker includes a lower surface and one or more third conductive connection dots on the lower surface, wherein the second group of one or more conductive connection dots on the upper surface of the first electronic sticker are configured to be in contact with the one or more third conductive connection dots on the lower surface of the second electronic sticker through the second window, the third window, and the fourth window.

13. The electronic sticker assembly of claim 11, further comprising:
a fourth electronic sticker over the first electronic sticker and on the side of the second electronic sticker, wherein the first electronic sticker comprises a third group of one or more conductive connection dots on the upper surface, wherein the fourth electronic sticker includes a lower surface and one or more fourth conductive connection dots on the lower surface, wherein the one or more fourth conductive connection dots are configured to be electrically connected with the third group of one or more conductive connection dots.

14. The electronic sticker assembly of claim 11, further comprising:
a third adhesive layer between the first electronic sticker and the fourth electronic sticker layer.

* * * * *